US006306581B1

(12) United States Patent
Koeffler et al.

(10) Patent No.: US 6,306,581 B1
(45) Date of Patent: Oct. 23, 2001

(54) DIAGNOSTIC ASSAY METHOD AND KIT FOR THE DETECTION OF HHV-8 INFECTION

(75) Inventors: H. Phillip Koeffler, Los Angeles; Jonathan W. Said, Sherman Oaks, both of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/409,616

(22) Filed: Oct. 1, 1999

Related U.S. Application Data

(62) Division of application No. 09/068,714, filed as application No. PCT/US98/01483 on Jan. 27, 1998, now Pat. No. 6,156,498.
(60) Provisional application No. 60/036,985, filed on Jan. 30, 1997.

(51) Int. Cl.[7] .............................. C12Q 1/70; C12Q 1/68; C07H 21/04
(52) U.S. Cl. .................. 435/5; 435/6; 435/7.94; 536/23.72
(58) Field of Search .................. 435/5, 6, 7.94; 536/23.72

(56) References Cited

U.S. PATENT DOCUMENTS

| | | |
|---|---|---|
| 5,801,042 | 9/1998 | Chang et al. . |
| 5,830,759 | 11/1998 | Chang et al. . |
| 5,831,064 | 11/1998 | Chang et al. . |
| 5,849,564 | 12/1998 | Chang et al. . |
| 5,853,734 | 12/1998 | Chang et al. . |
| 5,854,398 | 12/1998 | Chang et al. . |
| 5,854,418 | 12/1998 | Chang et al. . |
| 5,859,225 | 1/1999 | Chang et al. . |
| 5,861,240 * | 1/1999 | Ganem et al. ............... 435/5 |
| 5,861,500 | 1/1999 | Chang et al. . |
| 5,863,787 | 1/1999 | Chang et al. . |
| 5,908,773 | 6/1999 | Cesarman et al. . |

OTHER PUBLICATIONS

Ablashi, D. V. et al., Human Herpesvirus (HHV–8) Epidemiology and Characterization of Virus from KS–1 Cell Line, National AIDS Malignancy Conference, *Jounal of Acquired Immune Deficiency Syndromes and Human Retrovirology*, Vol. 14, No. 4, ABSTRACT 29, P. A23 (Apr. 1, 1997).

Ablashi, D. et al., Seroprevalence of human herpesvirus–8 (HHV–8) in countries of Southeast Asia compared to the USA, the Caribbean and Africa, *British Journal of Cancer*, 81(5):893–897 (1999).

Arvanitakis, L. et al., Establishment and Characterization of a Primary Effusion (Body Cavity–Based) Lymphoma Cell Line (BC–3) Harboring Kaposi's Sarcoma–Associated Herpesvirus (KSHV/HHV–8) in the Absence of Epstein–Barr Virus, *Blood*, Vol. 88, No. 7, pp. 2648–2654 (Oct. 1, 1996).

Cesarman, E. et al., Kaposi's Sarcoma–Asscoiated Herpesvirus–Like DNA Sequences in Aids–Related Body–Cavity–Based Lymphomas, *N. Engl. J. Med.*, 332(18): 1186–1191 (May 4, 1995).

Cesarman, E. et al., In Vitro Establishment and Characterization of Two Acquired Immunodeficiency Syndrome–Related Lymphoma Cell Lines (BC–1 and BC–2) Containing Kaposi's Sarcoma–Associated Herpesvirus–Like (KSHV) DNA Sequences, *Blood*, vol. 86, No. 7, pp. 2708–2714 (Oct. 1, 1995).

Chatlynne, L. et al., HHV–8 ELISA Using Whole Virus Lysate to Detect KS Antibodies in Human Sera, 4th Conference on Retroviruses and Opportunistic Infections, Washington, D. C. (Jan. 22–26, 1997) Poster 697, p. 193.

Chatlynne, L. G. et al., HHV–8 ELISA Using Whole Virus Lysate to Detect KS Antibodies in Human Sera, , *Advanced Biotechnologies, Incorporated*, 9108 Guilford Rd., Columbia, MD. (1997).

Chatlynne, Louise G. et al., Detection and Titration of Human Herpesvirus–8–Specific Antibodies in Sera From Blood Donors, Acquired Immunodeficiency Syndrome Patients, and Kaposi'Sarcoma Patients Using a Whole Virus Enzyme–Linked Immunosorbent Assay, *Blood*, vol. 92, No. 1, pp. 53–58, (Jul. 1, 1998).

Cozen, Wendy et al., Seroprevalence of Kaposi's Sarcoma–Associated Herpes Virus Antibody in Young Adult Hodgkin's Disease, *Blood*, vol. 81, No. 2, p. 724 (Jan. 16, 1998).

Drexler, H. H. et al., Lymphoma cells lines: in vitro models for the study of HHV–8 + primary effusion lymphomas (body cavity–based lymphomas), *Leukemia*, 12:1507–1517(1998).

Hermine, O. et al., Body–Cavity–Based Lymphoma in an HIV–Seronegative Patient Without Kaposi's Sarcoma–Assocoiated Herpesvirus–Like DNA Sequences, N. Engl. J. Med., p. 272, Jan. 25, 1996.

Lapps, W. J. et al., Purification, Molecular Characterization, and Ultrastructural Analysis of HHV–8 from a Body Cavity Lymphoma Cell Line, KS–1, Advanced Biotechnologies, 9108 Guilford Rd., Columbia, MD. (1997), Poster 696.

Lapps, W. J. et al., Purification, Molecular Characterization, and Ultrastructural Analysis of HHV–8 from a Body Cavity Lymphoma Cell Line, KS–1 4th Conference on Retroviruses and Opportuinistic Infections, Washington, D. C., (Jan. 22–26, 1997) Poster 696, p. 193.

Nador, R. g. et al., Herpes–like DNA Sequences in a Body–Cavity–Based Lymphoma in an HIV–Negative Patient, *N. Engl. J. Med.*, 399(14):943, Oct. 5, 1995.

(List continued on next page.)

Primary Examiner—Ali R. Salimi
(74) Attorney, Agent, or Firm—Sidley & Austin

(57) ABSTRACT

A method establishes for the first time a HHV-8 producing immortalized lymphoma cell line, which is free of EBV, CMV, and HIV. Large quantities of uncontaminated HHV-8 are produced by the cells, and the virus or immunogenic fragments thereof are used to obtain specific polyclonal and monoclonal antibody. Assays and kits are useful for detecting viral infection in mammalian samples.

3 Claims, No Drawings

OTHER PUBLICATIONS

Pinkus, G. S. et al., Immunohistochemical Detection of Epstein–Barr Virus–encoded Latent Membrane Protein in Reed–Sternberg Cells and Variants of Hodgkin's Disease, *Modern Pathology*, 7(4):454–461 (1994).

Rady, Peter et al., Detection of HHV–8 DNA in Kaposi's Sarcomas from Immunoisuppressed Patients, *Journal of Acquired Immune Deficiency Syndromes and Human Retrovirology*, vol. 14, No. 4, Abstract 28, p. A23 (Apr. 1, 1997).

Renne, R. et al., Lytic growth of Kaposi's sarcoma–associated herpesvirus (Human herpesvirus 8) in culture, *Nature Medicine*, 2(3):342–346 (Mar. 1996).

Said, J. W. et al., Kaposi's Sarcoma–Associated Herpesvirus (KSHV or HHV8) in Primary Effusion Lymphoma: Ultrastructural Demonstration of Herpesvirus in Lymphoma Cells, *Blood*, vol. 87, No. 12, pp. 4937–4943 (Jun. 15 1996).

Strauchen, J. A. et al., Body Cavity–Based Malignant Lymphoma Containing Kaposi Sarcoma–Associated Herpesvirus in an HIV–Negative Man with Previous Kaposi Sarcoma, *Ann. Intern. Med.*, 125(10):822–825 (Nov. 15, 1996).

Whitman, J. E. et al., HHV–8 (KSHV) Infected KS–1 Cell Line: Biological and Molecular Characterization of the Virus for Immuno–diagnostic and Therapeutic Applications, Second International Conference on Human Herpesviruses 6, 7 and 8 (May 8–11, 1997).

Parravicini, Carlo et al., Kaposi's Sarcoma–Associated Herpesvirus Infection and Multiple Myeoloma, *Science*, vol. 278, pp. 1969–1970 (Dec. 12, 1997).

Masood, Rizwan et al., Kaposi's Sarcoma–Associated Herpesvirus Infection and Multiple Myeoloma, *Science*, vol. 278, pp. 1970–1971 (Dec. 12, 1997).

Whitby Denise et al., Kaposi's Sarcoma–Associated Herpesvirus Infection and Multiple Myeoloma, *Science*, vol. 278, pp. 1971–1972 (Dec. 12, 1997).

Cottoni, Francesca et al., Kaposi's Sarcoma–Associated Herpesvirus Infection and Mulitple Myeoloma, *Science*, vol. 278, p. 1972 (Dec. 12, 1997).

Brousset, P. et al., Kaposi's Sarcoma–Associated Herpesvirus Infection and Multiple Myeoloma, *Science*, vol. 278, p. 1972 (Dec. 12, 1997).

Rettig, M. B. et al., Kaposi's Sarcoma–Associated Herpesvirus Infection and Multiple Myeoloma, *Science*, vol. 1972–1973, (Dec. 12, 1997).

* cited by examiner

DIAGNOSTIC ASSAY METHOD AND KIT FOR THE DETECTION OF HHV-8 INFECTION

This application is a division of U.S. patent application Ser. No. 09/068,714, filed May 14, 1998, now U.S. Pat. No. 6,156,499, which claims the benefit of International Application No. PCT/US98/01483, filed Jan. 27, 1998, and the benefit of U.S. Provisional Application No. 60/036,985, filed on Jan. 30, 1997.

BACKGROUND OF THE INVENTION

1. Field of the Invention

The present invention relates to a lymphoma cell line capable of producing large to quantities of Kaposi's sarcoma-associated herpes virus (KSHV or HHV-8), which are substantially free from human immunodeficiency virus (HIV), Cytomegalovirus (CMV) and Epstein-Barr Virus (EBV). This invention also relates to a method and kit for detecting HHV-8 infection.

2. Description of the Background

Kaposi's sarcoma (KS) is a rare neoplasm of multi focal origin characterized by red-purple to blue-brown lesions of the skin. Cell proliferation occurs initially in the skin, eventually spreading to other body sites, in particular to the lower extremities. Lymphatic involvement is not unusual in KS patients, and may be present as a lymphadenopathy. Kaposi's sarcoma is the most frequent neoplastic manifestation of HIV infection, and is used as one of the criteria to decide whether an HIV-infected individual is defined as having Acquired Immunodeficiency Syndrome (AIDS).

Four different epidemiologic forms of KS have been described: sporadic or classic KS, endemic KS, KS encountered among transplant recipients receiving immunosuppressive therapies, and KS prevalent among patients with human immunodeficiency virus (HIV) infection. The "classic" form of KS was described over a century ago in predominantly elderly men of Mediterranean and Jewish descent. Men are affected by this form of KS 10 to 15 times more often than women, and those affected are typically in their 60s or older, and have an average survival time of approximately 10 years. The "endemic" form of KS has been recognized in certain geographic regions of Central Africa. This is a neoplasm which also affects men more frequently than women, is generally more aggressive than classic KS, and involves the lymph nodes and viscera, as well. A marked increase in the form of KS encountered in patients receiving immunosuppressive therapy, was mostly found in hepatic and renal transplant patients. AIDS patients have a probability of about 40% of developing cancer, especially Kaposi's sarcoma and/or non-Hodgkin's lymphoma. Kaposi's sarcoma has, additionally, been associated with lymphoid cancer in patients both with and without AIDS.

Epidemiologic studies conducted with classic KS, endemic KS, and transplant patients suggest that both the infectious agent and the immune status of the individual are of significance in acquiring KS. The unidentified infectious agent, presumably the causative agent, has been referred to as Kaposi sarcoma-associated herpes virus (KSHV) and human herpes virus-8 (HHV-8), interchangeably. Two novel DNA fragments were found in 90% of KS lesions associated with AIDS. The isolation and identification of these DNA fragments from the KS lesions of an AIDS patient, designated KS330 and KS631, suggested the involvement of an infectious agent. The base sequences of the two DNA fragments, and their flanking sequences were shown to have significant homology with two known herpes viruses: herpes virus saimiri and Epstein-Barr Virus (EBV). The latter two viruses belong to the gammaherpesvirinae subfamily, whose members have the ability to replicate in lymphoblastoid cells. Of all members of the subclass, EBV is the best studied. EBV has been shown to induce latent infection of peripheral blood lymphocytes in its natural host, and to immortalize lymphocytes in vitro, thereby causing the development of malignant lymphomas such as endemic Burkitt's lymphomas, AIDS-related non-Hodgkin's lymphomas and lymphoproliferative disorders which occur after transplantation. A subset of non-Hodgkin's lymphomas, referred to as body cavity-based lymphomas BCBLs, or primary effusion lymphomas (PELs), present unique clinical, morphologic, immunophenotypic, and molecular genetic characteristics. BCBLs, for instance, grow mainly in the pleural, pericardial, and abdominal cavities, usually without an identifiable tumor mass. The cytomorphologic features of BCBLs appear to bridge large-cell immunoblastic and anaplastic large-cell lymphomas. Their cells are large and possess moderate to abundant amphophilic to deeply basophilic cytoplasm, and large, round to ovoid nuclei containing one or more large nucleoli. The lymphomas have indeterminate (non-B, non-T cell) immunophenotypes, and commonly express CD45 in the absence of other B or T cell lineage-restricted antigens. At the molecular level, the lymphomas are characterized by a B-cell genotype, as determined by clonal immunoglobulin gene rearrangements, and the absence of c-myc gene rearrangement.

As the numbers of reported AIDS cases increased, a concomitant rise in the incidence of KS was observed. This increase in KS has led to an increased effort to determine the pathogenesis of the neoplasm. The unavailability of a model system, however, has hindered these efforts.

The noticeable structural homology between EBV and KSHV has led to the hypothesis that KSHV might also be a transforming agent. In addition, KSHV/HHV-8 sequences were demonstrated in AIDS-related lymphomas, even in the absence of KS symptoms, but could not be detected in most non-AIDS-related lymphoid neoplasms. Since no source of HHV-8 free of other viruses was available, all cell lines established from neoplasms obtained from the HIV-infected individuals failed to provide, and could not be used as, a model system for KSHV/HHV-8, due to co-infection by other viruses, particularly EBV.

Herpes viruses as a group establish latent infections for the entire lifetime of their host. Their DNA genomes are relatively large, 100–250 kb, and may exist extra chromosomally in latently infected cells. The activation of an herpes virus results in viral replication, and eventually in cell lysis, with the viral copy number increasing substantially from the latent to the lytic infection stages. The latent stages of HSV in general, and KSHV in particular, infection produce no symptoms. The infected individuals, however, are still capable of transmitting the virus, and infecting others. Thus, although the KSHV/HHV-8 is present in the blood of seemingly healthy, yet infected, subjects, at present there are no acceptable methods to monitor the blood supply for HHV-8 infection.

Clearly, thus, up to the present time, the isolation and characterization of KSHV has been hampered because all cell sources have been co-infected with EBV, CMV, and/or HIV. Thus, the availability of a ready, abundant, and uncontaminated source of KSHV/HHV-8 would permit the systematic monitoring of blood bank stocks as well as of new blood donors to avoid the spread of the virus. In addition, it would permit the development of specific antibodies, and to conduct further pathogenicity studies.

SUMMARY OF THE INVENTION

The present invention, thus, relates to the isolation for the first time of a lymphoma cell line producing large quantities of Kaposi sarcoma-associated herpes virus (KSHV/HHV-8), which is substantially uncontaminated with human immunodeficiency virus (HIV), Cytomegalovirus (CMV) and/or Epstein-Barr Virus (EBV).

This invention also relates to a method for establishing lymphoma cells, as immortalized cell lines, and cell cultures producing copious quantities of KSHV/HHV-8.

The present invention also relates to the HHV-8 virus, free of viral contamination, produced by the lymphoma, and to antibody selectively binding HHV-8.

This invention also relates to methods and kits for screening for HHV-8 infection, with the aid of purified HHV-8 virus and/or antibody binding the virus. These products are useful in assays and kits for the detection of HHV-8 infection.

DESCRIPTION OF THE PREFERRED EMBODIMENTS OF THE INVENTION

The present invention arose from a desire by the inventors to develop a system for the easy and copious production of HHV-8 for application to the mass screening of biological samples for HHV-8 infection, for example for monitoring blood bank stocks, and newly donated blood and their donors. The availability of such screening system will, in turn, permit the ready separation and discarding of contaminated blood and blood product samples and, thus, help prevent further dissemination of HHV-8 infection, and of all diseases associated with it.

This invention, thus, provides for the first time a method of establishing an HHV-8 infected immortalized (established) lymphoma cell line, which is free from infection with the Epstein Barr virus (EBV), cytomegalovirus (CMV) and/or Human Immunodeficiency Virus (HIV), an HHV-8 producing cell line produced by this method, a method for producing copious amounts of virus in the substantial absence of cell lysis, and HHV-8 virus, produced by the cell line of the invention.

"KS-1" is one HHV-8 infected cell line produced in accordance with the invention.

"HHV-8", as used herein, means human herpes virus-8, which is synonymous with KSHV, Kaposi sarcoma-associated herpesvirus. HHV-8 is a gamma-2 herpesvirus (genus rhadinovirus), and is the first member of this genus known to infect humans.

The phrases "body-cavity based lymphoma" or "primary effusion lymphoma" (PEL), as used herein, refer to a lymphoma that is characterized as a primary lymphomatous effusion occurring in the pleural, pericardial, and/or abdominal cavity, usually in the absence of an identifiable tumor mass. Those skilled in the art will recognize the interchangability of other terms used to describe such lymphomas, such as, but not limited to, primary effusion lymphomas, KSHV-associated lymphomas, and the like.

The term "pleural fluid", as used herein, means an exudative fluid localized to the thoracic cavity. Pleural fluid may be collected by thoracentesis, i.e., puncturing the chest wall with a needle and collecting the pleural fluid in a syringe by aspiration. Similar fluid may be obtained from other serous cavities, e.g., peritoneum, pericardium, and the like.

The term "mammal", within the context of this invention, refers to any mammal capable of being infected with HHV-8, such as mouse, rat, rabbit, non-human primates, and humans, among others. In a preferred embodiment the mammal is a human.

The term "appropriate growth medium" means, as used herein, a medium comprising one or more substances that promote the growth of viable cells. Suitable growth media include, for example, RPMI, Minimum Essential Medium Eagle (MEM), and the like. The growth media are typically supplemented with fetal bovine serum (FBS) at a concentration of up to about 20%. Antibiotics, such as penicillin, streptomycin, and the like, may also be added to the media to inhibit bacterial infections. In a preferred aspect of the invention, the FBS is carefully preselected, as is known in the art, for its ability to allow the growth of blood cells, and their progenitors.

The term "ascites-inducing amount" means, as intended herein, a sufficient number of cells to produce a marked accumulation of serous fluid within a reasonable time in the ascitic cavity of a mammal. Typically, ascites fluid may be induced within about three weeks. In one embodiment of the invention, the ascites fluid is induced within about 6 weeks, preferably within about 3 weeks, and in some instances within about 5 days being especially preferred.

The term "immunocompromised animal", as used herein, means an animal with an impaired immune system such that it is incapable of fully reacting immunologically to pathogens. Those skilled in the art will recognize that this may be due to a genetic disorder, disease process, irradiation or drugs, such as corticosteroids or immunosuppressive agents, given to treat a disorder that inhibits immune function. Examples of genetic disorders which inhibit immune function include X-linked severe combined immunodeficiency, Nezelof's syndrome, Wiskott-Aldrich syndrome, leukocyte adhesion deficiency, and the like. Disease processes which inhibit immune function include disorders such as primary or secondary bone marrow failure, lymphomas and other malignant tumors, acquired immunodeficiency syndrome, and the like, prevent proper function of the immune system. Examples of drugs that suppress the immune system are methotrexate, cyclophosphamide, 6-mercaptopurine, vincristine, and the like. Suitable immunocompromised animals for use in the practice of the present invention are the nude mouse, SCID mouse, BNX immunodeficient mouse, and the like. A most preferred embodiment of the immunocompromised mammal is the triple-immunodeficient BNX mouse.

The term "immunogenic portion or fragment" means any unique portion of the virus capable of stimulating an immunological response, i.e., eliciting an antibody response.

The term "antibody", as used herein, is intended to include fragments thereof, as is known in the art, which also selectively bind HHV-8, including any unique portion of the virus. The antibody fragments may be obtained by fragmenting the entire antibody using conventional techniques, and the fragments screened in the same manner as described above for whole antibodies. For example, "F(ab')$_2$" fragments may be generated by treating an antibody with pepsin or papain, and "Fab" fragments may be obtained by treatment of the F(ab')$_2$ fragment with a reducing agent to reduce the disulfide bridges.

As used herein, the phrase "antigenic component" means either KS-1 cells, HHV-8 virus, antibody binding HHV-8, and the like.

The phrase "sample" as used herein refers to any biological fluid, such as whole blood, plasma, or other bodily fluids or tissues having either HHV-8 or anti-HHV-8 antibodies, preferably serum, and the like.

The present invention also provides a method for establishing immortalized lymphoma cells, such as KS-1, in culture. The method comprises culturing a sample from a fluid, such as pleural, ascitic, or pericardial fluid, obtained from a body cavity of a subject afflicted with a body cavity-based lymphoma (BCBL), or primary effusion lymphoma (PEL), in an appropriate growth medium as a primary isolate or culture, injecting an ascites-inducing amount of the primary isolate or culture into an immunocompromised animal, isolating cells from the ascitic fluid of the immunocompromised animal, and culturing the isolated established cells in an appropriate growth medium. The cell lines obtained herein demonstrate an enhanced ability to grow in culture as compared with cells that have not been injected into immunocompromised animals, i.e., cells from the primary isolate or culture.

Also provided herein is a method for growing large amounts of, isolating, and purifying the HHV-8 virus obtained from the cell line of the invention. The method generally comprises growing a lymphoma cell line prepared by the method of this invention in a growth medium, allowing the cells in culture to produce large amounts of HHV-8 virus, and separating the virus from the cells and/or the medium. Suitable purification methods are well known to those skilled in the art. (See, for example, B. Roizman, R. J. Whitley, and C. Lopez (eds.), Human Herpes viruses, Raven Press Limited, N.Y. (1993)). The separation may be attained by, for example, but is not limited to, centrifugation, and the purification to affinity separation with the aid of antibody selectively binding to it. Other methods may also be utilized.

The purified virus obtained from the cells of this invention, e.g., the KS-1 cell line, constitutes at least about 85%, more generally at least about 90%, or in some instances at least about 95%, by weight of the material isolated from the cells. In other words, the purified virus of the present invention contains no greater than about 15% impurities, i.e., non-viral particles, preferably no greater than about 10% impurities, and most preferably no greater than about 5% impurities. The purified virus is, however, substantially free of contamination with other viral particles, and generally has an isopycnic sucrose density of about 1.15 g/cm$^3$. The HHV-8 virus of this invention has been shown to contains only human sequences and is, therefore, considered to be free of contamination with materials from other species, including murine sequences.

The purified virus, being free of contamination from other viruses in general, and particularly from HIV, CMV, and EBV, is particularly suitable for the preparation of antibodies selectively binding HHV-8, or an immunogenic fragment thereof. For example, anti-serum or monoclonal antibodies which selectively bind the virus or one of its fragments, may be obtained by methods known in the art using the an attenuated form of the entire virus, an immunogenic fragment or a capsid protein thereof. Briefly, a mammal, such as, a mouse, hamster, or rabbit, may be immunized with an immunogenic form of HHV-8, such as an inactivated HHV-8, a capsid protein, and the like. The technology for conferring immunogenicity on a protein or peptide are known in the art. For example, the protein or peptide may be administered in the presence of an adjuvant to enhance and amplify its immunogenicity. Furthermore, once obtained, the polyclonal or monoclonal antibodies of the present invention may be used to isolate, and further purify naturally occurring HHV-8. Those of skill in the art will readily identify suitable adjuvants for use herein, given that such materials are well known in the art. Following effective immunization, HHV-8 anti-serum may be obtained and, if desired, polyclonal anti-HHV-8 antibodies isolated therefrom. Hybridoma cell lines secreting monoclonal antibodies (mAbs) selectively binding the HHV-8 virus may be obtained by the Kohler and Milstein technology, and other techniques, such as the EBV-hybridoma technique to produce human monoclonal antibodies, and the human B-cell hybridoma technique. Briefly, antibody producing cells, i.e., lymphocytes, are harvested from an animal immunized as described above, and fused by, for example, standard somatic cell fusion procedures with immortalizing cells, such as myeloma cells, preferably of non-producing myeloma cells, to yield the immortalized hybridoma cells. Such techniques are well known in the art. (Kohler & Milstein, Nature (1975) 256: 495–497; Cole et al., Monoclonal Antibodies & Cancer Therapy (1985) Alan R. Less, Inc., pp. 77–96; Kozbar, et al., Immunology Today (1983) 4:72). The thus obtained hybridoma cells may then be immunochemically screened for the production of antibodies selectively binding the isolated HHV-8, or a portion or fragment thereof, and the monoclonal antibodies isolated by affinity separation.

The antibodies of the invention selectively binding HHV-8 or portions or fragments thereof may also be utilized as a tool in diagnostic assays, which are suitable for application to all tissues, such as a biopsy, or to a fluid sample, such as, serum, obtained from a subject. Highly specific serological tests are of extreme value in, for example, screening populations for HHV-8 infected subjects, monitoring the blood bank supplies, and the like. The utilization of the present diagnostic method and kit, will lead to ensuring, for the first time, a safe, i.e., HHV-8-free, blood supply which, in turn, will reduce the likelihood of transmission of the virus.

The methods for detecting HHV-8 infection in a sample, in accordance with this invention, are varied, and include those relying on the detection of the virus or a portion thereof, and those relying on the detection of antibody elicited by viral infection. The overall methods rely on known technologies, such as immunohistochemistry, in situ hybridization, fluorescent in situ hybridization, radioimmunoassay, and the like, and may include labels such as radiolabels, enzymes, fluorescent, and phosphorescent labels, and the like (DeLuca, "Immunofluorescence Analysis", in Antibody as a Tool, Marchalonis et al., eds., John Wiley & Sons, Ltd., pp 189–231 (1982), the relevant portions of which are incorporated herein by reference). One method for detecting the presence of antibody-bound complexes employs an "ELISA"-type assay, that relies on the detection and quantification of either antibody or antigen (depending on the ELISA format type) present in a sample. ELISA assays are a well-known techniques that may be readily carried out by those having ordinary skill in the art (Chapter 22, 4th Edition of Basic and Clinical Immunology, D. P. Sites et al., Lange Medical Publication, CA (1982), the relevant portions of which being incorporated herein by reference). ELISA assays employed in the practice of the present invention include the use of the antibody and/or virus of this invention, or of fragments of either one or both, or of the cell line of the invention, preferably bound to a solid matrix or support which, as is well known in the art, are water insoluble and include crosslinked dextran (Pharmacia Fine Chemicals; Piscataway, N.J.), agarose, polystyrene beads (typically about 1 micron to about 5 millimeters in diameter (Abbott Laboratories, Chicago, Ill.), cellulose, polyvinyl chloride, polystyrene, crosslinked polyacrylamide, nitrocellulose- and nylon-based webs such as sheets, strips or paddles, or tubes, plates, or wells of a microtiter plate, such as those made from polystyrene or polyvinylchloride, and the like. The antibodies of the invention may be labeled, to facilitate the identification of HHV-8 or antibody selectively binding the virus in a sample, with a variety of detectable compounds. The detectable label may be a fluorescent labeling agent that chemically binds to the antibody without producing denaturation to form a fluorochrome (dye) useful as an immunofluorescent tracer. Suitable fluorescent labeling agents include fluorochromes, such as fluorescein isocyanate (FIC), fluorescein isothiocyanate (FITC), 5-dimethylamino-1-naphthalenesulfonyl chloride (DANSC), tetramethylrhodamine isothiocyanate (TRITC), lissamine, rhodamine 8200 sulphonyl chloride, and the like. Radioactive atoms are also useful detectable labels for antibodies, including those which produce gamma ray emission, such as $^{125}$I and $^{131}$I. The antibody label may also be an enzyme, such as horseradish peroxidase (HRP), glucose oxidase, alkaline phosphatase, and the like. In this case, e.g., HRP or glucose oxidase, additional reagents are typically required to indicate that an antibody-antigen complex has formed, which include hydrogen peroxide, and an oxidation dye precursor such as o-phenylenediamine dihydrochloride, diaminobenzidine, and the like. An additional reagent useful with glucose oxidase is 2,2'-azino-di-(3-ethyl-benzthiazoline-G-sulfonic acid), and one useful with alkaline phosphatase is para-nitrophenyl phosphate. Depending on the nature of the label or catalytic signal producing system used, the produced signal may be detected by irradiating the complexed test sample with light of the correct wavelength and observing the level of fluorescence, by contacting the complexed sample with a substrate which may be catalytically converted by the label to produce a dye, fluorescence, phosphorescence, or chemiluminescence, in which the formation of dye may be observed visually or in a spectrophotometer, by employing a radiation counter such as a gamma counter to detect gamma emitting labels such as $^{125}$I, and the like.

The methods described above, and others as well, may be practiced with the kits of this invention for detection of HHV-8 infection in a subject using anti-HHV-8 antibodies described herein. The kits which, in accordance to the invention, may be applied in the detection of HHV-8 infection may contain, for example, the antibodies described above, monoclonal or polyclonal, or their fragments, which selectively bind HHV-8 or a portion therof, which may be conjugated to a fluorochrome, a phosphochrome, enzyme, or radiolabel, an appropriate substrate for enzyme-linked antibodies, e. g., hydrogen peroxide for a peroxidase, blocking solutions, e.g., normal goat or rabbit serum, 3% bovine serum albumin in physiological saline, and the like, and buffers, e.g., Tris-HCl, phosphate buffered saline, EDTA, and the like, among others, as well as combinations of any two or more thereof.

The HHV-8 obtained by the method of the invention may also be utilized in a kit for diagnosing HHV-8 infection in a subject. The substantially pure HHV-8 of this invention may be attached to a solid support, and contacted with the blood or blood product of a subject, to detect any antibodies selectively binding to HHV-8 present in the subject's blood or blood product, by binding to the immobilized HHV-8, and the bound complex detected with, e.g., a labeled secondary antibody such as anti-human IgG, fragments thereof, or protein A or G. Another kit provided herein is useful for the detection of anti-HHV-8 antibodies in a sample, and may contain the virus or an antigenic component thereof, immobilized onto a slide or microtiter plate, anti-human antibodies or fragments thereof, or protein A or G, buffers, and a detectable (labeled or to be labeled) secondary antibody. The secondary antibodies, polyclonal and preferably monoclonal, useful in the practice of the present invention may be obtained by techniques well known in the art. The polyclonal antibodies may be obtained, for example, by the methods in Ghose et al., Methods of Enzymology, 93, 326–327 (1983). with IgG or Fe fragments of IgG being used as the immunogen to stimulate the production of IgG-reactive polyclonal antibodies in the antisera of non-human animals, such as rabbits, goats, sheep, rodents, and the like. Depending on the secondary antibody or label used, the kits may optionally contain a signal generating substance to provide or enhance the detection of the anti-HHV-8 antibodies. Suitable substrates for enzymatic signal generation systems, include simple chromogens and fluorogens such as para-nitrophenyl phosphate, hydrogen peroxide, and the like. In addition to the above, other components such as ancillary reagents may be included, for example, stabilizers, buffers, e. g., Tris-HCl, phosphate buffered saline, EDTA, and the like, fixatives, and the like. The reagents may be provided as dry powders, usually lyophilized, including excipients, which on dissolution will provide a reagent solution having the appropriate concentrations for performing the methods of the present invention.

The invention will now be described in greater detail by reference to the following non-limiting examples. The relevant portions of all references, patents, and published patent applications cited throughout this application are hereby incorporated by reference.

EXAMPLES

Example 1

Establishment of KS-1 Cells in Culture

Cells from the pleural fluid from a subject manifesting primary KSHV-positive effusion-based lymphoma were obtained by thoracentesis and grown in RPMI plus 20% bovine serum at 37° C. in 5% carbon dioxide and air. The cells began to proliferate actively within 3 days of initial in vitro culture. Cells grew nonadherently, occasionally in small clumps, and had a cellular doubling rate of about 48 to 72 hours.

Cells from the above described in vitro cultures were separated from the growth medium by centrifugation, washed 3 times, and resuspended in saline. The resuspended cells ($4 \times 10^6$ cells total) were injected into the peritoneal cavity of triple-immunodeficient BNX mice (supplied by Harland Sprague-Dawley in Cambridge, Mass.), who developed prominent ascites within 3 weeks of injection.

Ascitic fluid was collected from the mice, centrifuged, washed, and resuspended in RPMI containing 20% fetal bovine serum (Gibco, BRL, Gaithersburg, Md.). The cells grow non-adherently with a doubling time of approximately 48 hours.

Example 2

Immunophenotypic Characterization of KS-1 Cells

Immunophenotypic studies were performed using antibodies and/or in situ hybridization probes to immunoglobulin kappa and lambda chains, CD3, CD20, CD45, CD79a (DAKO Corporation, Carpinteria, Calif.), CD5 (Becton-Dickinson Immunocytometry Systems, Mountain View, Calif.), CD56 (N-CAM; Bender Med-Systems, Vienna, Austria), Herpes simplex virus types 1 and 2, EBV latent membrane protein (LMP-1), and EBV EBER1 (DAKO).

These immunophenotypic studies showed KS-1 cells to be positive for CD45 and CD20, but negative for surface IgGs, for T-cell markers (CD3 and CD5), for CD56

(N-CAM), and for DC79a. The B-cell lineage was confirmed by the demonstration of clonal rearrangements of the Ig gene in Southern blots. In addition, the cells express recognizable human karyotipic abnormalities, and the requisite cell surface antigens. The cells obtained from the murine ascitic fluid stained positively for cytoplasmic light chains, and were negative for EBV as evidenced by immunohistochemistry for EBV latent membrane protein (LMP-1), and in situ hybridization for Epstein-Barr encoded RNA (EBER). The cells were also negative for CMV, as determined by in situ hybridization, and for herpes simplex virus 1 and 2, as determined by immunohistochemistry.

Example 3

Purification of HHV-8

KS-1 cells are collected by centrifugation for 10 minutes at 1,500 rpm, resuspended in 1:20 vol of culture medium, and snap-frozen to obtain a cell virus extract. A supernatent containing the virus is obtained by centrifugation of a 1,400×g cleared conditioned culture medium for 2 hours at 23,000×g at 4° C., and the pellets are then resuspended in 1:50 vols of culture medium and snap-frozen. Both preparations, cell and supernatent virus, are then thawed, sonicated to rupture the cell membrane, cleared by centrifugation at 10,000×g at 4° C., loaded on a phosphate-buffered saline-25% sucrose cushion, and pelleted by overnight centrifugation at 70,000×g at 4° C. The viral pellets are resuspended in PBS and prepared for further use.

Example 4

Immobilization of KS-1 Cells on Glass Slides

The cells present in the cell suspension are counted using a microscope and hemacytometer, and resuspended in a sufficient volume of buffer to achieve 5×105 cells per ml. A sufficient volume is added to each slide so that 50,000–100,000 cells are applied to each slide.

The cells were centrifuged in a Cytospin 3™ (Shandon, Inc. Pittsburgh, Pa.) at 500 rpm for 5 minutes to apply 0.01 ml of the resuspended cells to each slide. Cytospins are air dried for 10 minutes. The cells are then fixed to the slide by incubation for 2 minutes in sufficient volume of ice cold methanol/acetone (50/50) to cover the sample, and the slide is then allowed to air dry. The slides may be stored at −20° C.

Example 5

Immunofluorescence Assay

Four slides prepared in accordance with Example 4 are used for each serum sample. Each slide is thawed, transfered to 1×PBS, blocked by incubation with 3% BSA in PBS for 30 minutes, and washed 3 times in PBS, 10 minutes per wash. The slides are then dried with a Cytospin filter.

The serum to be tested is serially diluted 1:10, 1:40, and 1:160 with PBS containing 10% rabbit serum, 2% BSA and 1% glycine, and each dilution is applied to only one slide. Only a secondary antibody is applied to the fourth slide, which is then used as a control.

50 µl of each of the dilutions of the human serum are added to the appropriate slide, and only the secondary antibody to the control slide. The samples are incubated for 90 minutes at room temperature in sufficient humidity to prevent volume loss. The sera are rinsed off with two 10 min. washes in PBS containing 0.4% Tween® 20, and one 10 min. wash in PBS, and the slides are dried with a Cytospin filter. 50 82 1 rabbit anti-human IgG FITC antibodies (secondary antibodies) (DAKO) are added at a 1:40 dilution in PBS to each slide, and the samples are incubated for 45 minutes at room temperature, in sufficient humidity to minimize volume loss. The slides are then rinsed three times with PBS containing 0.4% Tween® 20, and one drop of Aquamount is applied onto the slides, and then a coverslip. The slides are stored at −20° C. in a light tight box until ready to read.

The fluorescence is read under a fluorescence microscope at 400× magnification at an excitation wavelength is 495 nm, and an emission wavelength is 525 nm.

Example 6

Enzyme-linked Immunosorbent Assay

50 µl human sera are diluted as desired with PBS containing 10% rabbit serum, 2% BSA, and 1% glycine, and added to each slide prepared in accordance with Example 4 by immobilizing KS-1 cells. 50 µl PBS with albumin are added to blank slides. All samples are allowed to stand at room temperature for one hour, in sufficient humidity to minimize volume loss, the serum is aspirated, and the samples are washed three times with 50 µl of PBS containing 0.02% sodium azide (NaN3) and 0.05% Tween®.

50 µl of an alkaline phosphatase-coupled goat anti-human IgC antibody in PBS containing 0.25% bovine serum albumin is then added to each slide, the optimal dilution being pre-determined using a standard titration assay. Goat F(ab')$_2$ anti-human IgG(Fc)-alkaline phosphatase may be obtained from Jackson Immuno-Research Laboratories in West Grove, Pa. The samples are incubated for 60 to 90 minutes at room temperature in sufficient humidity to minimize volume loss, and the samples washed three times with a sufficient volume of PBS containing 0.02% sodium azide (NaN3) and 0.05% Tween® to cover the cells. All samples are then washed three more times with TRIS-NaCl solution containing 0.05M Tris, 0.15M NaCl, and 0.02% sodium azide, pH 7.5, and 0.75 g disodium p-nitrophenol phosphate (United States Biochemicals catalogue #19587 or AMRESCO catalogue #P0364) is combined with a Tris buffer containing 75 mM Tris-HCl, 1.5 mM MgCl2, 0.02% sodium azide, pH 8.6 to form a substrate containing solution, 50 µl of which are added to each slide. The samples are incubated at room temperature for about 30 to 90 minutes in sufficient humidity to minimize volume loss, and the slide read at 405 nm.

The KS-1 cell line was deposited with the American Type Culture Collection (ATCC), 12301 Parklawn Drive, Rockville, Md., U.S.A. 20852, on Dec. 18, 1996, under the terms of the Budapest Treaty on the International Recognition of Deposits of Microorganisms for Purposes of Patent Procedure and the Regulations promulgated under this Treaty. The KS-1 cell line has been given ATCC Accession No. CRL-12247. Samples of the deposited material are, and will be made, available to industrial property offices and other persons legally entitled to receive them under the terms of the Treaty and Regulations and, otherwise, in compliance with the patent laws and regulations of the United States of America and all other nations or international organizations in which this application, or an application claiming priority of this application, is filed, or in which any patent is granted on any such application. In particular, all restrictions upon the availability of the deposited material will be irrevocably removed upon issuance of a U.S. patent based on this, or any application claiming priority to, or incorporating this application by reference thereto.

Those having ordinary skill in the art will recognize, or be able to ascertain using no more than routine experimentation, numerous equivalents to the specific procedures described herein. Such equivalents are considered to be within the scope of this invention and are covered by the following claims.

What is claimed is:

1. An assay method for detecting antibody selectively binding HHV-8, comprising:

contacting with HHV-8 viral particles a serum sample originating from an individual suspected of having an HHV-8 infection, said HHV-8 viral particles having been produced by and isolated from immortalized lymphoma cells, wherein the cells are from a cell line deposited with ATCC as Accession No. CRL-12247, said lymphoma cells originating from cells isolated and cultured from ascitic fluid of an immunocompromised animal, said animal having previously received into its peritoneal cavity an inoculation of an ascites-inducing number of cells from a primary cell culture, said primary cell culture having been derived from the pleural fluid of a cavity-based lymphoma of a HHV-8$^+$ human, said human at the time of producing the pleural fluid being HIV$^-$, CMV$^-$, and EBV$^-$;

allowing the formation of complexes of the antibody and the HHV-8 viral particles;

contacting any antibody-bound HHV-8 complexes thus formed with anti-human antibody-binding immnunoglobulin or anti-human antibody-binding fragments thereof, said fragments being selected from the group consisting of Fab and F(ab')$_2$, and allowing the formation of complexes of the immunoglobulin or the fragments thereof with the antibody-bound HHV-8 complexes; and detecting the presence of any complexes formed.

2. An anti-HHV-8 antibody detecting kit, comprising:

HHV-8 viral particles, said HHV-8 viral particles having been produced by and isolated from immortalized lymphoma cells, wherein the cells are from a cell line deposited with ATCC as Accession No. CRL-12247, said lymphoma cells originating from cells isolated and cultured from ascitic fluid of an immunocompromised animal, said animal having previously received into its peritoneal cavity an inoculation of an ascites-inducing number of cells from a primary cell culture, said primary cell culture having been derived from the pleural fluid of a cavity-based lymphoma of a HHV-8$^-$ human, said human at the time of producing the pleural fluid being HIV$^-$, CMV$^-$, and EBV$^-$; and labeled anti-human antibody-binding immunoglobulin or labeled anti-human antibody-binding fragments thereof selected from the group consisting of Fab and F(ab')$_2$.

3. The anti-HHV-8 antibody detecting kit in accordance with claim 2, further comprising:

a solid matrix for supporting said HHV-8 viral particles.

* * * * *

UNITED STATES PATENT AND TRADEMARK OFFICE
CERTIFICATE OF CORRECTION

PATENT NO. : 6,306,581 B1
DATED : October 23, 2001
INVENTOR(S) : H. Phillip Koeffler and Jonathan W. Said It is certified that error appears in the above-identified patent and that said Letters Patent is hereby corrected as shown below:

Column 11,
Lines 22-23, please delete "immnunoglobulin" and insert therefor -- immunoglobulin --.

Column 12,
Line 17, please delete "HHV-8$^-$" and insert therefor -- HHV-8$^+$ --.

Signed and Sealed this

Twenty-first Day of May, 2002

Attest:

Attesting Officer

JAMES E. ROGAN
Director of the United States Patent and Trademark Office